United States Patent [19]
Morein et al.

[11] Patent Number: 5,679,354
[45] Date of Patent: Oct. 21, 1997

[54] MATRIX WITH IMMUNOMODULATING ACTIVITY

[76] Inventors: Bror Morein, Ollonstigen 3 Vreta, S-755 90 Uppsala; Karin Lövgren, Lindsbergsgatan 8C, S-752 40 Uppsala, both of Sweden; Kristian Dalsgaard, Ny Vordingborgvej 80, DK-4771 Kalvehave, Denmark; Jan Thurin, 28 University News, Philadelphia, Pa. 19104-4756; Bo Sundquist, Bellmansgatan 30, S-754 28 Uppsala, Sweden

[21] Appl. No.: 671,816

[22] PCT Filed: Sep. 28, 1989

[86] PCT No.: PCT/SE89/00528

§ 371 Date: May 21, 1991

§ 102(e) Date: May 21, 1991

[87] PCT Pub. No.: WO90/03184

PCT Pub. Date: Apr. 5, 1990

Related U.S. Application Data

[63] Continuation of Ser. No. 251,576, Sep. 30, 1988, abandoned.

[30] Foreign Application Priority Data

| Mar. 22, 1989 | [SE] | Sweden | 8901027 |
| Aug. 16, 1989 | [SE] | Sweden | 8902780 |

[51] Int. Cl.$^6$ .......................... A61K 47/08; A61K 45/00
[52] U.S. Cl. .................................. 424/278.1; 514/25
[58] Field of Search ................ 424/88, 92, 278.1; 514/25

[56] References Cited

U.S. PATENT DOCUMENTS

| 4,101,652 | 7/1978 | Bonati | 424/49 |
| 4,578,269 | 3/1986 | Morein | 424/88 |
| 4,806,350 | 2/1989 | Gerber | 424/88 |
| 5,057,540 | 10/1991 | Kensil et al. | 514/25 |
| 5,182,109 | 1/1993 | Tamura et al. | 424/92 |

FOREIGN PATENT DOCUMENTS

| 0231039 | 8/1987 | European Pat. Off. | A61K 39/39 |
| WO88/09336 | 12/1988 | WIPO | C07J 17/00 |

OTHER PUBLICATIONS

Higuchi et al., Phytochemistry 26:229–235 (1987).
Higuchi et al., Phytochemistry 26:2357–2360 (1987a).
"Studies on the Cellular Site of Action of the Adjuvant Activity of Saponin for Sheep Erythrocytes", *Int. Archs Allergy appl. Immun.*, vol. 67, 1982, By R. Bomford, pp. 127–131.
"The Requirement of Lipids for the Formation of Immunostimulating Complexes (Iscoms)", *Biotechnology and Applied Biochemistry*, vol. 10, 1988, By K. Lovgren et al., pp. 161–172.
"Saponin and Other Haemolysins (Vitamin A, Aliphatic Amines, Polyene Antibiotics) as Adjuvants for SRBC in the Mouse" *Int. Archs Allergy appl. Immun.*, vol. 63, 1980, By R. Bomford, pp. 170–177.
"Incorporation of the Major Outer Membrane Protein of Neisseria gonorrhoeae in Saponin–Lipid Complexes (Iscoms): Chemical Analysis, Some Structural Features, and Comparison of Their Immunogenicity with Three Other Antigen Delivery Systems", *Infection and Immunity*, vol. 56, No. 2, Feb. 1988, By G. Kersten et al., pp. 432–438.
"Saponin Adjuvants", *Archiv fur die gesamte Virusforschung*, vol. 44, 1974, By K. Dalsgaard, pp. 243–254.
"Triterpenoid Saponins as Antiulcer Agents", *Chemical Abstracts* vol. 108, No. 20, May 1988, By Y. Muto et al., p. 398.

*Primary Examiner*—Michael P. Woodward
*Attorney, Agent, or Firm*—Young & Thompson

[57] ABSTRACT

The invention claims an iscom matrix which is not a lipid vesicle comprising at least one lipid and at least one saponin but no intentional antigenic determinants and optionally also adjuvants for use as an immunomodulating agent, medicines, vaccines, kits containing the matrix and new saponins, and a process for preparing the new saponins. The invention also concerns a process for preparing the matrix characterized in that at least one sterol is solubilized in a solvent or detergent, the saponin or saponins are added, the other adjuvants and lipids are optionally also added, whereafter the organic solvent or the detergent may be removed for example with dialysis, ultra filtration, gel filtration or electrophoresis. The sterol and saponin might also be solubilized in the lipids and/or adjuvants.

10 Claims, 12 Drawing Sheets

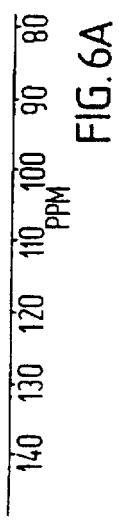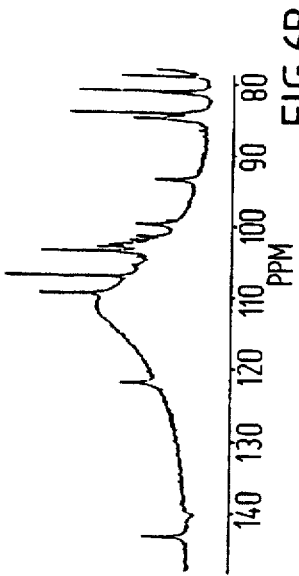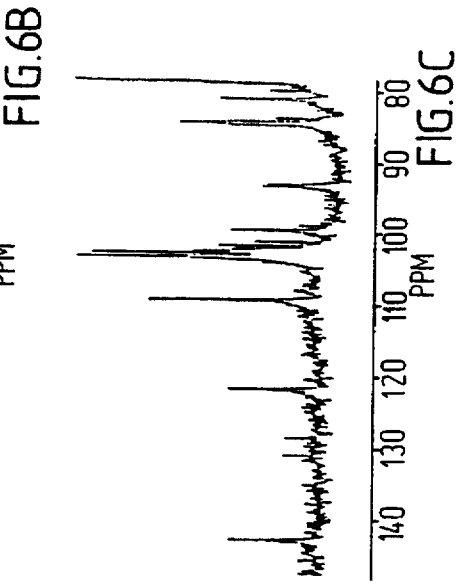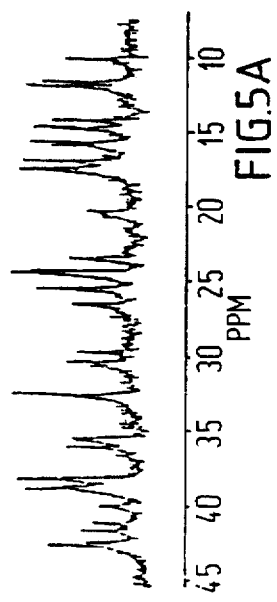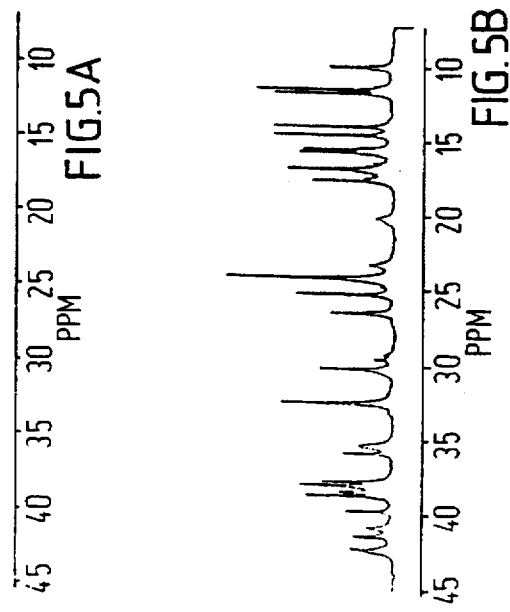

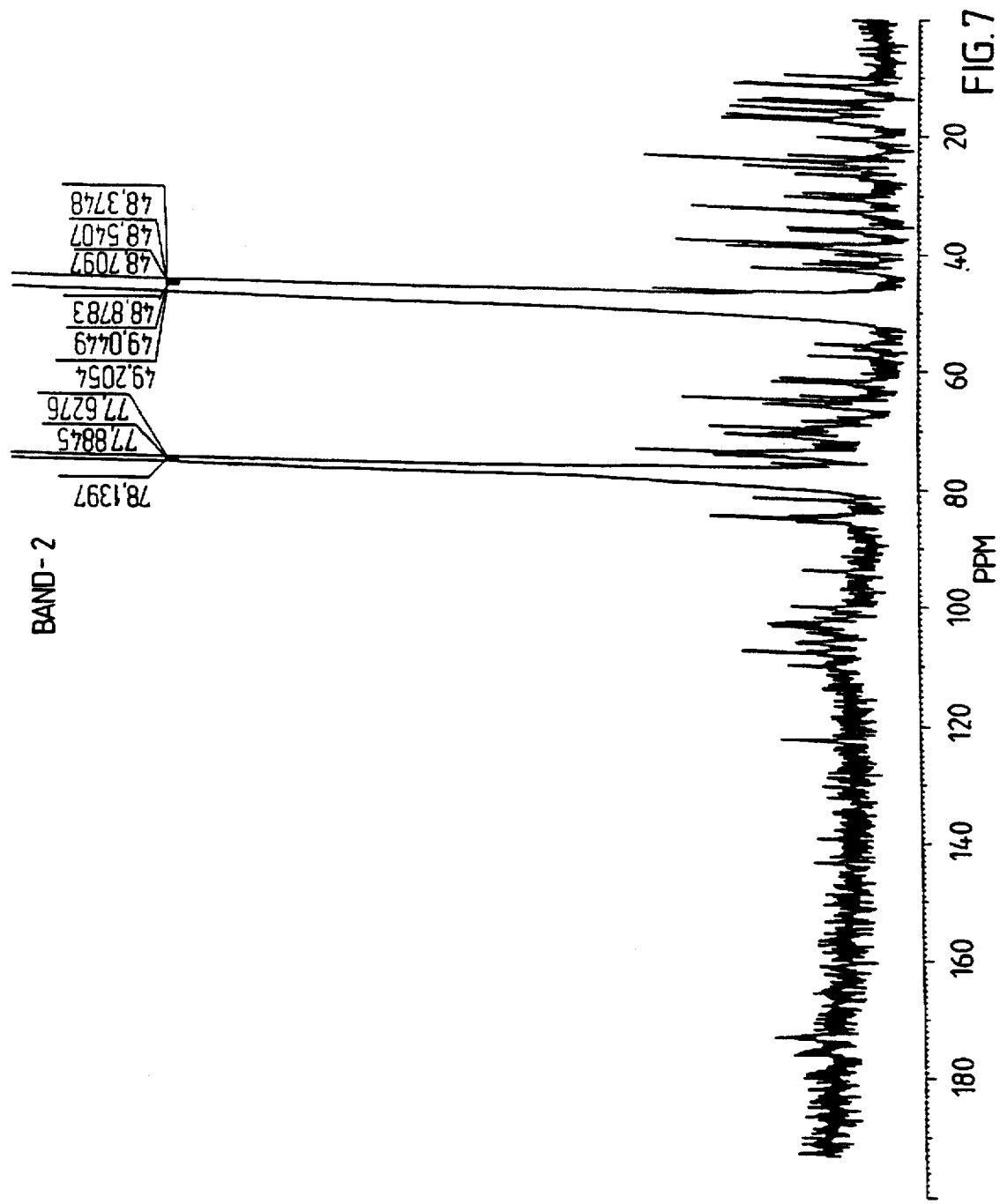

MATRIX WITH IMMUNOMODULATING ACTIVITY

This is a continuing application of Ser. No. 07/251,576 which was filed on Sep. 30, 1988, and now abandoned.

The present invention concerns an iscom matrix comprising at least one lipid and at least one saponin with immunomodulating effect, a process for preparing the matrix, a vaccine and a kit comprising the same and new saponins for incorporation in the matrix and a process for preparing the new saponins.

Many microbial and vital antigens can be produced by modern techniques today. Their full promise in vaccines will however not be realized unless they are administered along with an effective adjuvant, an agent that increases antibody and/or cell-mediated immune responses.

The only adjuvants currently authorized for human use in most countries are aluminum hydroxide and aluminum phosphate which have been used for many years to increase antibody responses to e.g. diphtheria and tetanus toxoids. Although these adjuvants are sufficient for many vaccines, studies have shown that other adjuvants, e.g. Freund's complete adjuvant (FCA), and Quil A often are more efficacious in eliciting antibody response and cell-mediated immunity in experimental animals. In fact, they are frequently required for protection. However, FCA produces granulomas at injection sites, which makes them unacceptable for human and veterinary vaccines. In fact, even aluminum hydroxide may give rise to reactions in form of granuloma at the injection site. For these reasons, many attempts are made to develop adjuvants with the efficacy of FCA but without undesirable side effects.

In Morein's EPC Patent Applications Nos. 83850273.0 and 85850326.1, there are described immunogenic complexes between antigenic determinants with hydrophobic regions and glycosides, among them triterpensaponins and especially Quil A, so called iscom complexes. In such an iscom, the amount of Quil A can be about 10–100 times lower and produce the same antigenic effect as when Quil A in free form is mixed with the antigen.

European Patent Application 87200035.1 indicates that the presence of antigen is not necessary for formation of the basic iscom structure, this being possible to form from a sterol, such as cholesterol, a phospholipid, such as phosphatidylethanolamine, and a glycoside such as Quil A.

It has now been discovered that a phospholipid is not needed for the preparation of the basic iscom structure including no antigen. Instead a sterol, such as cholesterol in conjunction with a glycoside such as Quil A are the essential structural components assembled into a complex resembling the typical cage-like iscom structure, so called matrix. It has also turned out that the matrix has immunomodulating effects such as adjuvant or immunosuppressive effect.

The present invention concerns a complex between at least one lipid such as a sterol, preferably cholesterol, and one or more saponins, such as triterpensaponins, especially Quil A or subcomponents thereof which is not a lipid vesicle without any intentional antigens or antigenic determinants for use as an immunomodulating agent. Thus, there is not integrated any antigenic component as is done in an iscom. This matrix has adjuvant effect and can be used mixed together with one or more antigens preferably in multimeric form.

In this iscom matrix there is also possible to integrate other adjuvants with hydrophobic regions. Addition of other lipids may be required to facilitate the inclusion of other adjuvants. Thus the present invention also concerns a complex containing lipids and adjuvants, other than cholesterol and saponins. Such complexes contains the matrix consisting of cholesterol and saponin, preferably Quil A or subcomponents thereof, one or more other adjuvants and one or more lipids other than cholesterol. These are preferably not lipid vesicles or liposomes and have a very special structure in electron microscopy.

Liposomes have been described in the literature and their general structure is well known to biological research workers. Liposomes are vesicles comprising one or more series of lipid layers forming onion-like structures spaced one from another by aqueous material.

The matrix can be injected in an animal or human being as a mixture with the antigen in multimeric form. Alternatively the matrix and the antigen can be injected separately. In this case the best results are obtained if the adjuvant matrix and the the antigen are injected in regions which are drained into the same lymphatic gland. When the adjuvant is presented in multimeric form in a matrix according to the invention the dose of adjuvant may be lowered as compared with when the adjuvant is injected separately in monomeric form or in an undefined form. This implies that toxic side effects caused by adjuvants when used conventionally, i.e. when they are injected alone as such, can be lowered or avoided. The dose of adjuvant can, however, not be lowered as much as is done in the iscom complexes according to the above mentioned patent applications.

When an adjuvant is used in a matrix according to the invention, the antigen is not integrated in the same particle as the adjuvant as is done in an iscom particle according to the above mentioned EPC Patent Applications. This implies that one can use antigens without amphiphatic properties or antigens which can not be forced to expose hydrophobic regions. As an example it can be mentioned that some viruses do not have amphiphatic proteins, e.g. picornavirus, adenovirus or parvovirus, but they have a form of submicroscopic particle with the antigen presented in several copies, i.e. as multimers.

For such viruses it is more practical to inject them together with the new adjuvant complex than to couple hydrophobic groups to them or create hydrophobic groups by other means (e.g. partial denaturation) and integrate them into an iscom particle.

Typically, the present matrix contains sterol, preferably cholesterol, and one or more saponins in a molar ratio of about 1 to 1 or in a weight ratio of about 1 to 5. The complexes have an open sperical structure consisting of circular subunits or parts of the spherical structure revealed by electron microscopy. They have a sedimentation coefficient of about 20 S.

When other adjuvants are integrated, the lipid-adjuvant-matrix typically contains sterol and saponin in a molar ratio of about 1:1 and the other adjuvants and lipids together make up to about 1 molar. For such a matrix the molar ratio of sterol; saponin; other adjuvant and lipids is about 1:1:1. Thus the molar ratio of sterol; saponin; other adjuvant and other lipids is 1:1:0,1–1; 0,1–1, i.e. additional lipid or adjuvant may be present in the matrix until its molar ratio (or the sum of their molar ratios) is a half that of the saponin and sterol present.

The structure as revealed by electron microscopy is the same as for iscom and matrix (see FIG. 1).

The sedimentation coefficient, being dependent on the density of material incorporated into the matrix, is about 12–22 S for matrices containing cholesterol, saponin, other adjuvants and lipids.

The saponins can be any saponin with hydrophobic regions such as those described in R Tschesche and Wulf, Chemie und Biologic der Saponine in Fortschritte der Chemie Organischer Naturstoffe, published by W Herz, H, Grisebach, G W Kirby, Vol 30 (1973), especially the strongly polar saponins, primarily the polar triterpensaponins such as the polar acidic bisdesmosides, e.g. saponin extract from Quillsjabark Araloside A, Chikosetsusaponin IV, Calendula-Glycoside C, Chikosetsusaponin V, Achyranthes-Saponin B. Calendula-Glycoside A, Araloside B, Araloside C, Putranjia-Saponin III, Bersamasaponiside, Putrajia-Saponin IV, Trichoside A, Trichoside B, Saponaside A, Trichoside C, Gypsoside. Nutanoside, Dianthoside C, Saponaside D, preferably aescine from *Aesculus hippocastanum* (T Part and W Winkler: Das therapeutisch wirksame Prinzip der Rosskastanie (*Aesculus hippocastanum*), Arzneimittelforschung 10(4), 273–275 (1960) or sapoalbin from *Gyposophilla struthium* (R Vochten, P Joos and R Ruyssen: Physico-chemical properties of sapoalbin and their relation to the foam stability, J Pharm Belg 42, 213–226 (1968), especially saponin extract from *Quillaja saponaria* Molina, primarily the DQ-extract which is produced according to K Dalsgaard: Saponin Adjuvants, Bull Off Int Epiz 77 (7–8), 1289–1295 (1972) and Quil A which is produced according to K Dalsgaard: Saponin Adjuvants III, Archiv f ür die Gesamte Virusforschung 44, 243–254 (1974). Quil A and subfragments thereof are preferred, especially the fragments B2, B3 and B4B described below.

The present invention also provides new glycosylated triterpenoid saponins derived from Quillaja Saponaria Molina of Beta Amytin type with 8–11 carbohydrate moieties which have the following characteristics:

a) Substance B2 has a molecular weight of 1988, a carbon 13 nuclear magnetic resonance (NMR) spectrum as indicated in FIGS. 5A and 6A and a proton NMR spectrum as shown in FIGS. 11A and 12A.

b) Substance B3 has a molecular weight of 2150 and has a carbon 13 NMR spectrum as shown in FIGS. 5B and 6B, and a proton NMR spectrum as shown in FIGS. 11B and 12B.

c) Substance B4B has a molecular weight of 1862, a carbon 13 NMR spectrum as shown in FIGS. 5C and 6C, and a proton NMR structure as shown in FIGS. 11C and 12C.

Compounds B2 and B3 have adjuvant activity in their own right. The present invention also relates therefore to the use of these compounds as adjuvants. Compound B4B is of use in the preparation of an iscom matrix. B2 and B3 having adjuvant activity can be included in the matrix.

Matrix can be produced from a sterol such as cholesterol and the saponin B4B. Such a matrix does not seem to have any potent adjuvant activity. In order to potentiate the adjuvant activity in this matrix, it is possible and even preferable to integrate the saponins B2 and/or B3 and/or any other substance with adjuvant effect and with hydrophobic groups. If the adjuvants do not contain any hydrophobic groups such groups might be coupled to them by use of known chemical methods. If other adjuvants than B2 or B3 are to be integrated, there are preferably incorporated further lipids as listed hereinafter.

In the sterol-B4B matrix, it is also possible to integrate immunosuppressive substances containing hydrophobic groups or to which such groups have been coupled.

It is also possible to use the sterol-B4B matrix as an immunomodulating agent in mixture with adjuvants, immunosuppressive substances or antigens or mixtures thereof.

As immunodulating agents are considered substances that enhance, suppress or change the immune system such as adjuvants, suppressors, interleukins, interferons or other cytokins.

The invention preferably concerns an matrix containing a sterol, especially cholesterol, B4B and either of B2 and B3 or both. When matrix is prepared from cholesterol and Quil A, it comprises B2, B3 and B4B.

The matrixes can be produced by solubilizing at least one sterol in a solvent, adding the saponin or saponins, and possibly the other adjuvants and lipids, whereafter the solvent might be removed and the matrix transformed into a solution where its components are not soluble, e.g. a water solution. This can be done with gel filtration, ultra filtration, dialysis or electrophores. The matrices may then be purified from excess of sterol and Quil A e.g. by centrifugation through a density gradient, or gel filtration. As solvent there might be used water or the solubilizing agents or detergents mentioned below.

The only limiting factor for matrix formation to take place is the time needed in different physico-chemical environments, the major rate limiting factor being the poor solubility of the sterol, e.g. cholesterol, in water, in which the matrix forming saponins are freely soluble.

Thus it has been shown that with Quil A and cholesterol even in solid phase matrix-like formation takes place after a relatively long time, e.g. about 1 month. Cholesterol must be brought into contact with Quil A or its purified components. If the cholesterol is brought into colloidal water suspension through treatment by ultrasonication and treatment by ultraturrax, matrix is formed with Quil A after about 12 hours.

Consequently, any other substance such as a detergent added to the water, and which will increase the solubility of cholesterol in the aqueous medium, will decrease the time needed for the formation of matrix. It is thus possible to produce a matrix from cholesterol, water and Quil A or the subcomponents thereof, if the cholesterol is brought to a colloidal form. It is, however, more practical to add a detergent or a solvent.

Preferably the saponins are used from a concentration of at least their critical micelle formation concentration (CMC). For Quil A this implies a concentration of at least 0.03% by weight.

As solubilizing agent there can be used detergents such as non-ionic, ionic i.e. cationic or anionic or Zwitter-ionic detergent such as Zwittergent or detergent based on gallic acid which is used in excess. Typical examples of suitable non-ionic detergents are N-alkanoyl-N-alkyl-glucamines, polyglycol esters and polyglycol ethers with aliphatic or aralylphatic acids and alcohols. Examples of these are alkylpolyoxyethylene ethers with the general formula $C_nH_{2n+1}(OCH_2CH_2)_xOH$, shortened to $C_nE_x$; alkyl-phenyl polyoxyethylene ethers containing a phenyl ring between the alkyl group and the polyoxyethylene chain, abbreviated $C_n\phi E_x$, Triton X-100=tert.-$C_8E_{9.6}$ (octylphenolether of polyethylene oxide), acylpolyoxyethylene esters: acylpolyoxyethylene sorbitane esters, abbreviated $C_n$ sorbitane $E_x$, e.g. Tween 20, Tween 80, β-D-alkylglucosides, e.g. β-D-octylglucoside. Typical examples of suitable ionic detergents are gallic acid detergents such as e.g. cholic acid, desoxycholate, cholate and CTAB (cetyltriammonium bromide). Even conjugated detergents such as e.g. taurodeoxyoholate, glycodeoxycholate and glycocholate can be used. Other possible solubilizing agents are lysolecithin and synthetic lysophosphoilipids. Even mixtures of the above-mentioned detergents can be used. When using the dialysis method the detergents should be dialysable in not too long time.

Some surface active substances greatly facilitate matrix formation. These include the intrinsic biological membrane lipids with a polar head group and a non-polar aliphatic chain e.g. phosphatidyl choline (negatively charged) and phosphatidyl ethanolamine (positively charged).

Solubilizing can also be performed with alcohols, organic solvents or small amphiphatic molecules such as heptane-1,2,3-triol, hexane-1,2,3-triol or caotrophic substances, acetic acid, such as trifluoro-acetic acid, trichloro-acetic acid, urea or quanidine hydrochloride.

Preferably to be used are ethyl alcohol, dioxane, ether, chloroform, acetone, benzene, acetic acid, carbon disulphid, MEGA-10 (N-decanoyl-N-methyl glucamine) and β-octylglucoside.

Various yields of matrix can be obtained with these substances, and the overall picture is that more matrix is formed the higher the concentration of the detergent is in the system.

It is technically possible to produce, purify, and sterilize matrix in any of the systems described. Therefore the adjuvant active technical preparations of matrix may contain solubilizing agents if their chemical nature and their concentration is acceptable in the final product, e.g. for vaccine purposes. However, in many cases, it will be necessary to remove the solubilizing agent from the matrix by dialysis, ultrafiltration or column chromatographic techniques. It is even possible to dilute the preparation until an allowed concentration of a given solubilizing agent or detergent is reached. The preparation is diluted with water or a physiologically acceptable solution preferably to a concentration below the CMC for the solubilizing agent or detergent in the system (the preparation) used.

The solubilizing agent might be incorporated in the matrix in a molar ratio of sterol saponin: further lipid adjuvants or solubilizing agent 1:1:1, i.e. molar ratio of the sum of lipid, adjuvants and solubilizing agent is up to half the molar that of saponin and sterol.

The solubilizing agent might alternatively be left mixed with the iscom matrix.

In order to be integrated the solubilizing agent and other immunomodulating components, should have at least one hydrophobic region. If not present such hydrophobic regions can be coupled to the components before the matrix is made.

Examples of adjuvants that can be incorporated in iscom matrix are any adjuvant, natural or synthetic, with desired immunomodulatory effect, e.g. muramyl dipeptide (MDP)-derivatives, such as fatty acid substituted MDP, threonyl analogs of MPD; amphipatic copolymers aliphatic amines such as avridine or DDA, poly anions such as Dextran sulphate, lipopolysaccarides such as saponins (other than Quil A). ("Future prospects for vaccine adjuvants", Warren, H. S. (1988) CRC Crit. Rev. Immunol. 8:2, 83–101; "Characterization of a nontoxic monophosphoryl lipid A", (1987) Johnson, A. G. et al, Rev. Infect. Dis. 9:5, 5512–5516; "Developmental status of synthetic immunomodulators", Berendt, M. J. et al (1985), Year Immunol. 193–201: "Immunopotentiating conjugates", Stewart-Tull, D. E., Vaccine, 85, 3:1, 40–44).

These four references are hereby incorporated as references.

The following Zwitterionic, neutral, positive and negative detergents are examples of detergents that have immunomodulating, especially adjuvant activity:

Nonionic block polymer surfactants containing hydrophilic polyoxyethylene (POE) and hydrophobic polyoxypropylene (POP) that differed in mol weight percentage of POE and mode of linkage POP to POE (BASF Wyandotte Corp.), such as L72, L81, L92, pluronic L101, L121, 2531 and 31R1: octablocks T1501; B-D-octylglucosid; cationic surfactants such as dimethyldioctadecylammonium bromide (DDA), octadecylamine (OCT), and cetyltrimethylammonium bromide (CTAB); maltostose tetrapalmirate, trehalose monomycolate, trehalose dibehenylbehenate: zwittergent detergents (N-alkyl-N,N-dimethyl-ammonio-3-propanesulphonate) Z3–8, Z3–10, Z3–12, Z3–14, Z3–16, obtained from Calbiochem (La Jolla, Calif., USA); Z3–18 obtained from Serra (Heidelberg, FRG), Myrj 45, Brij 52, Brij 58 (also from Serva), and dioctylsulphosuccinate and Tween 20, Tween 80, Triton X-100 and sodium deoxycholate.

These detergents can be used as both detergents and adjuvants and be incorporated in the iscom matrix.

The following are examples of immunosuppressive agents that can be incorporated in a sterol (preferably cholesterol) B4B matrix: cyclosporin A, diodecyl dimethyl ammonium bromide, cationic single chain amphiphiles with more than 10 carbon atoms and preferably more than 15 carbon atoms, double chain amphiphiles with up to 14 carbon atoms, preferably up to 12 carbon atoms.

In the case a desired adjuvant or immunosuppressive agent do not have suitable hydrophobic properties, it has to be modified to comprise a hydrophobic domain for incorporation into the matrix.

The hydrophobic group that can be coupled to non-hydrophobic adjuvants are straight, branched, saturated or unsaturated aliphatic chains having 1, 2, 3, 4, 5, 6, 7, 8, 9, 10, 11, 12, 13, 14, 15, 16, 17, 18, 19, 20, 21, 22, 23, 24 and 25 carbon atoms, such as lipids, preferably 6, 7 and 8 carbon atoms: small peptides with 1, 2, 3, 4 or 5 amino acids, preferably 2, 3, 4, selected from Trp, Ile, Phe, Pro, Tyr, Leu, Var, especially Tyr; choline acid, ursodesoxycholine acid or cholesterol derivatives.

These hydrophobic groups must be bonded to a group that can be coupled to the non-hydrophobic protein such as carboxyl-, amino-, disulphide-, hydroxyl-, sulphydryl- and carbonyl group, such as aldehyde groups.

As hydrophobic groups that can be coupled are selected preferably carboxyl, aldehyde, amino, hydroxyl, and disulphide derivatives of methane, ethane, propane, butane, hexane, heptane, octane and peptides containing Cys, Asp, Glu, Lys, preferably octanal and Tyr.Tyr.Tyr-Cys, -Asp or -Glu. The hydrophobic groups with a group that can be coupled must be dissolved in water with the aid of for example the solubilizing agents and detergents mentioned above or hydrochloric acid, acetic acid, 67% by volume acetic acid, caustic liquor, ammonia, depending on what substance is to be dissolved. pH is then adjusted to the neutral direction without the substance precipitating: here it is to make sure that there is not obtained a pH-value that denaturates the protein to which the hydrophobic group is to be coupled.

Hydrophobic groups with a carboxyl group as coupling molecule can be coupled to the adjuvants through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of trimethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrous acid can at low temperature be converted to diazonium salts, which gives azo bonds with Tyr, His and Lys.

The hydroxyl groups with succinic anhydride can be converted to hemisuccinate derivatives which can be coupled as carboxyl groups.

Aldehyde groups can be reacted with amino groups in the protein to a Schiff's base.

Several coupling groups and methods are described in Journal of Immunological Methods, 59 (1983) 129–143, 289–299, Methods in Enzymoloy Vol 93 pp 280–33, and in Analytical Biochemistry 116, 402–407 (1981) which are here incorporated as references.

The lipids other than sterol can be fats or fat resembling substances such as triglycerides or mixed triglycerides containing fatty acids with up to 50 carbon acids such as saturated fatty acids with 4, 5, 6, 7, 8, 9, 10, 11, 12, 13, 14, 15, 16, 17, 18, 19, 20, 21, 22, 23, 24, 25, 26, 27, 28, 29 and 30 carbon atoms e.g. burytic acid, caprole acid, caprylic acid, captic acid, lauric acid, myristic acid, palmitic acid, stearic acid, arachidic acid, behenic acid, lignoceric acid, or unsaturated fatty acids with up to 30 carbon atoms, such as hexadecene acid, oleic acid, linoleic acid, linolenic acid, arachidonic acid: hydroxy-fatty acids such as 9,10-dihydroxy stearic acid, unsaturated hydroxy fatty acids such as castor oil, branched fatty acids: glycerol ethers, waxes i.e. esters between higher fatty acids and monohydric alcohols: phospholipides such as derivatives of glycerol phosphates such as derivatives of phosphatidic acids i.e. lecithin, cephalin, inositol phosphatides, spingosine derivatives with 14, 15, 16, 17, 18, 19 and 20 carbon atoms: glycolipids isoprenoids, sulpholipids, carotenoids, steroids, sterols, cholestanol, caprostanol, phytosterols, e.g. stigmasterol, sitosterol, mycosterols, e.g. ergosterol, bile acids e.g. cholic acid, deoxycholic acid, chenodeoxycholic acid, litocholic acid, steroid glycosides, esters of vitamins A, or mixtures thereof.

These and other useful lipids are described in: Lipid biochemistry and introduction, Ed. M. I. Gurr, A. I. James, 1980, Chapman and Hall, London, New York, University Press Cambridge, which hereby is incorporated as a reference.

Preferably cholesterol phosphatidyleholine, liposomes or intralipid® (Oleum soya fractionate 200 g, Lechitinum fractionate vitello ovi 12 g, glycerol 22.5 g, and $H_2O$ up to 1 liter) are used.

The lipids can be added at any stage in the process, preferably before the addition of the saponin but lipids could also be added after the saponin.

The matrix is best produced by the dialysis method as follows.

Cholesterol dissolved in 20% MEGA-10 or any other suitable detergent, preferably a detergent that can be removed by dialysis, e.g. β-octylglucoside, (in $H_2O$ or a suitable buffer) is mixed with 5 times as much Quil A (solid or dissolved in water or a suitable buffer, e.g. PBS). The mixture is dialysed extensively against PBS, first over night at room temperature (because MEGA-10 will precipitate at +4° C.), then at +4° C. The matrixes are purified from excess Quil A and cholesterol by pelleting through e.g. 30% (w/w) sucrose (e.g., a TST 41.13 rotor 18 h, 39,000 rpm, 10° C.). The pelleted matrixes are dissolved in PBS (or any other suitable buffer) and the concentration adjusted to 1 mg/ml).

The present matrix can be used as an immunomodulating substance. It can be used as a potentiating agent for an immunosuppressive substance or an adjuvant, either mixed therewith or integrated in the matrix.

A matrix containing a sterol such as cholesterol, saponins, adjuvants and optionally further lipids can be used as an adjuvant. It can be used for potentiating the antigenic effect of any antigen or antigenic determinants from any pathogenic organism or any fragments or subunits of, or derived from these. Thus it can be used as an adjuvant for those antigens that are integrated in an iscom. Such antigens are mentioned in the EPC-patent applications 83850273.0 and 85850326.1, which are hereby incorporated as references. Thus the matrix can be used as adjuvants together with antigens or antigenic determinants derived from viruses with or without envelope, bacteria, protozoa, mycoplasmas, helminths, mollusca or together with such whole organisms. The antigenes or antigenic determinants might further be hormones, enzymes, carbohydrates and carbohydrate-containing structures such as lipopolysaccharides, peptides or proteins or recombinants thereof.

The present invention thus also covers human or veterinary medicine, characterized in that it comprises at least one matrix and one or more antigenic or immunosuppressive substances and a pharmaceutically acceptable vehicle in mixture or in separate compartments.

The invention also concerns a vaccine comprising an matrix, one or more antigens and a pharmaceutically acceptable vehicle.

Further the invention concerns a kit comprising such a medicine or vaccine.

In some medicines or vaccines the detergent used when preparing the matrix can be present if the detergent is allowed for the product in question.

The effect of the new adjuvant complex according to the invention will now be described in immunostimulating experiments.

1. Comparison between the immunogenic effects from antigens presented as iscoms, micelles or micellas plus the new matrix.

Mice were immunized with envelope protein from influenza virus in the form of iscom complex, micelles and micelles together with the new complex according to the invention (so called matrix). The immune response was evaluated by measuring the antibodies with ELISA technique 15, 30, 44 and 50 days after injection. The following injections were made:

1. 5 µg Micelle+0.1 µg matrix were mixed and injected in the left foreleg.
2. 5 µg Micelle+0.1 µg matrix injected separately in the right and left foreleg respectively.
3. 5 µg Micelle
4. 5 µg iscom prepared according to EPC 83850273.0

TABLE 1

| DAY | 1 | 2 | 3 | 4 |
|---|---|---|---|---|
| 15 | 23.700 ± 9.500 | 12.900 ± 14.500 | 18.900 ± 9.500 | 41.600 ± 1.000 |
| 30 | 30.800 ± 10.500 | 8.800 ± 7.100 | 9.800 ± 3.600 | 80.700 ± 21.700 |
| 44 | 30.000 ± 17.600 | 32.600 ± 17.300 | 17.900 ± 4.200 | 129.00 ± 78.400 |
| 50 | 309.300 ± 89.000 | 136.700 ± 103.700 | 87.600 ± 18.200 | 880.430 ± 295.500 |

No side effects in the form of local reactions were noted.

From this experiment one can conclude that envelope protein from influenza in the form of iscom or micelles plus matrix gives the highest antibody titres. Matrix can be presented in a very low dose and still have adjuvant effect. In order to get an adjuvant effect in mice, Quil A in free form is required in a dose a 100 times the dose of matrix, 10 µg. With that dose Quil A begins to give local side reactions. In order for matrix to have an obvious adjuvant effect the antigen in multimeric form should be injected in the same region e.g. leg as the matrix, i.e. the injected adjuvant matrix complex and antigen should be presented in a region, that is drained to the same lymphatic gland.

2. Comparison between the immunogenic effects from envelope protein from influenza in the from of iscom or micelle with or without matrix or diphtheria toxoid (DT).

Mice were injected with envelope protein in the following forms:
1. 5 µg Iscom+5 µg DT
2. 5 µg Iscom
3. 5 µg micelle
4. 5 µg micelle+0.1 µg matrix The antibody response in envelope proteins was estimated in the serum with ELISA-technique. The following results were obtained:

TABLE 2

| DAY | 1 | 2 | 3 | 4 |
|---|---|---|---|---|
| 15 | 52.800[1] | 48.300 | 8.400 | 29.000 |
| 30 | 119.202 | 155.567 | 22.107 | 87.000 |
| 50 | 110.600 | 136.200 | 33.400 | 96.500 |
| 65 | 1.691.000 | 3.783.000 | 283.300 | 1.149.000 |
| 80 | 562.800 | 2.529.000 | 512.300 | 976.500 |

[1]ELISA-titer where the last dilution gives a significant positive value at 450 nm.

No visible side effects in form of local reactions could be noted.

One can conclude that envelope protein from influenza virus in the form of iscom or micelles plus the adjuvant complex (matrix) according to the invention gives the highest antibody titres. The dose of matrix can be kept very low, i.e. 0.1 µg, and still has a notable adjuvant effect.

3. Comparison between the immunogenic effects from diphtheria toxoid (DT) in monomeric form, monomeric DT+iscom containing envelope protein from influenza virus, monomeric DT in mixture with Quil A and cholesterol and monomeric DT+adjuvant complex (matrix) according to the invention.

In this experiment diphtheria toxoid is used as a model antigen in monomeric form.

Mice were injected with diphtheria toxoid in the following forms:
1. 5 µg DT (diphtheria toxoid)
2. 5 µg DT+5 µg iscom
3. 5 µg DT+0.5 µg Quil A+0.1 µg CL (cholesterol)
4. 5 µg DT+0.1 µg matrix

TABLE 3

| DAY | 1 | 2 | 3 | 4 |
|---|---|---|---|---|
| 15 | ≦30 | ≦30 | ≦30 | ≦30 |
| 30 | ≦30 | ≦30 | ≦30 | ≦30 |
| 50 | ≦30 | ≦30 | ≦30 | ≦30 |
| 65 | ≦30 | 90 | ≦30 | 10.000 |
| 80 | ≦30 | 60 | 90 | 1.10 |

The immungenic response to DT is low in all the groups. The best result is obtained with mice immunized with diphtheria toxoid plus matrix according to the invention.

From the experiments above one can conclude that the best results are obtained when the matrix according to the invention is used together with the antigen in multimeric form. The matrix according to the invention has thus proved to give very good results as adjuvant compared with e.g. Quil A in free form. Thus it is worth noting that Quil A is effective as adjuvant in free form in doses such as 10 µg for mice, 50 µg for guinea-pigs and 1 mg for cattles. A practical volume for injection of a vaccine is 1 ml for small animals and 2 to 5 or 10 ml for big animals. As CMC (the critical micelle concentration) for Quil A is 0.03%, 1 ml will imply an amount of 300 µg when 1 ml is injected. After injection, however, due to the dilution effect, the concentration will become lower than CMC and the micelle will become unstable.

According to the present invention, however, the saponin and especially the Quil A molecules will be bounded together with cholesterol molecules so that a relatively stable complex is formed at very low concentrations. This complex is effective as adjuvant in a dose, which corresponds to 0.1 µg Quil A, i.e. 100 times lower than when Quil A is presented in free form.

BRIEF DESCRIPTION OF THE DRAWINGS

The Figures show:

FIG. 5A shows the $^{13}$C-NMR-spectrum in a first region, for the new substance B2;

FIG. 5B shows the $^{13}$C-NMR-spectrum in a first region, for the new substance B3;

FIG. 5C shows the $^{13}$C-NMR-spectrum in a first region, for the new substance B4B;

FIG. 6A shows the $^{13}$C-NMR-spectrum in a second region, for the new substance B2;

FIG. 6B shows the $^{13}$C-NMR-spectrum in a second region, for the new substance B3;

FIG. 6C shows the $^{13}$C-NMR-spectrum in a second region, for the new substance B4B;

FIG. 7 shows the complete $^{13}$C-NMR-spectrum for the substance B2;

Figure 1:
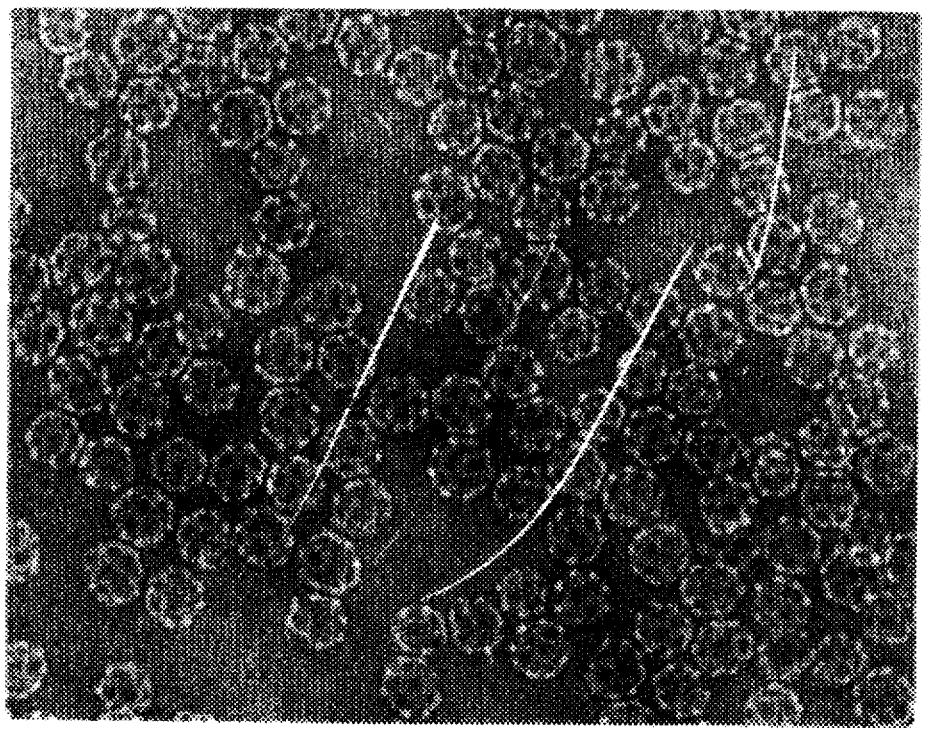
FIG. 1 shows an electron microscope picture of a typical matrix.

The invention will now be described further with the following example.

EXAMPLE 1

Matrix (Cholesterol-Quil A complex)

1 mg of cholesterol dissolved in 20% MEGA-10 (in $H_2O$) was mixed with 5 mg of solid Quil A. The Quil A was dissolved and the mixture was dialysed extensively against PBS, first over night at room temperature, then at +4° C. The iscom matrixes were purified from excess Quil A and cholesterol by pelleting through 30% (w/w) sucrose (TST 41.13 rotor 18 h, 39.000 rpm, 10° C.). The pelleted matrixes were dissolved in PBS and the concentration adjusted to 1 mg/ml (traced by a small amount of $H^3$-cholesterol).

EXAMPLE 2

MDP (muramyldipeptide, Sigma, adjuvant peptide) was conjugated to phosphatidyl ethanolamine (PEA) using N-ethyl-N'-(dimethylaminopropyl) carbodiimide hydrochloride as described by Lefrancier et al., 1977 (Lefrancier, P., Choay, J., Derrien, M. and Lederman, I. (1977) Int. J. peptide Protein Res. 9:249–257).

To 1 mg of cholesterol (in 20% MEGA-10 in $H_2O$) was added an equimolar amount of MDP-PEA (in MEGA-10 or DMSO or any other water miscible solvent), an equimolar amount of phosphatidyl choline and 7 mg of Quil A (a slight excess in comparison to 5 mg that is required for IM-formation). After a short incubation at room temperature (15–30 min) the mixture was extensively dialysed against PBS (room temperature 4–12 h, then at +4° C.).

After completed dialysis, the matrix-complexes with the additional adjuvant integrated were purified from excess Quil A by pelleting through 10% sucrose.

EXAMPLE 4

To 1 mg of cholesterol (in 20% MEGA-10 in $H_2O$). was added an equimolar amount of Avridine (N,N-dioctadecyl-N'N'-bis(2-hydroxyethyl)propenediamine (in MEGA-10 or DMSO or any other water micible solvent), an equimolar amount of phosphatidyl choline and 7 mg of Quil A (a slight excess in comparison to 5 mg that is required for IM-formation). After a short incubation at room temperature (15–30 min) the mixture was extensively dialysed against PBS (room temperature 4–12 h, then at +4° C.).

After completed dialysis, the matrix-complexes with the additional adjuvant integrated were purified from excess Quil A and adjuvant by pelleting through 10% sucrose (the same method as described on page 14, last paragraph).

EXAMPLE 4

To 1 mg of cholesterol (in 20% MEGA-10 in $H_2O$) was added an equimolar amount of DDA (dimethyl dioctadecyl ammonium bromide (in MEGA-10 or DMSO or any other water micible solvent), an equimolar amount of phosphatidyl choline and 7 mg of Quil A (a slight excess in comparison to 5 mg that is required for matrix-formation). After a short incubation at room temperature (15–30 min) the mixture was extensively dialysed against PBS (room temperature 4–12 h, then at +4° C.).

After completed dialysis, the matrix-complexes with the additional adjuvant integrated were purified from excess Quil A and adjuvant by pelleting through 10% sucrose (the same method as described on page 14, last paragraph).

EXAMPLE 5

2 g of Mega 10 is added to 10 ml of water before the addition of 200 mg cholesterol, and the cholesterol is dispersed by ultrasonication/ultraturrax. As much as 1.6 ml of this mixture can be added to the 10 ml of 2% Quil A-solution. The reaction mixture clarifies completely after less than one hour indicating that all the cholesterol has been reacted. It can be seen in the electron microscope that the concentration of matrix is very high even if the concentration of detergent in this case is 10%. Removal of the detergent by dialysis or ultrafiltration does not quantitatively affect the number of matrix particles, and the solution of matrix strays completely clear.

This experiment indicates that matrix formation takes place when the surfactants are present in the reaction mixtures, and that complete matrix formation takes place in very high concentrations of detergent.

EXAMPLE 6

Preparation of the Quil A components B2, B3 and B4B according to the invention.

5 g Cortex quillajae (Nordiske Droge of Kemikalieforretning, Copenhagen, Batch nr 8372) and 50 ml destillated water was mixed by a magnetical stirrer for 3 hours at room temperature. The liquid phase was separated through a Büchner funnel by a filter paper and was purified by filtering through a Metricel Gelman membrane 0.22μ. Such an extract contains 2.5% dry material.

The crude extract was dialysed against 200 volumes of destillated water in a Visking-tube without weld 20/32 for 48 hours with exchange of water after 24 hours. This extract is called DQ.

Figure 2:
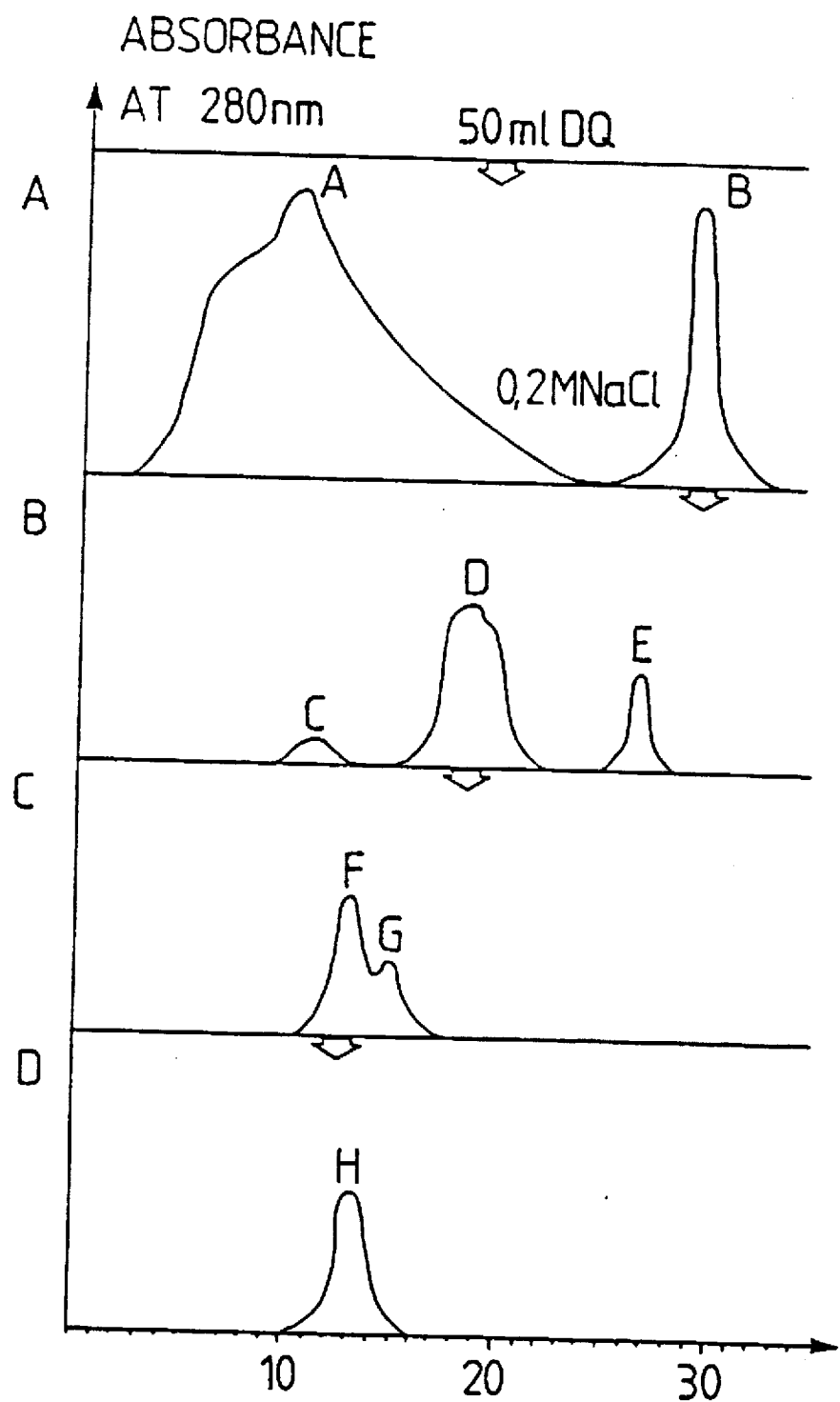
FIG. 2 shows U.V. eluation profiles for subfractions of Quil A.

The dialysed extract above was subjected to ion exchange chromatography. A column of DEAE-cellulose equilibrated with 0.1M Tris-HCl pH 7.5 was prepared (Whatman DE52) in a K 9/15 column (Pharmacia Fine Chemicals). The bed material was equilibrated with 0.1M Tris-HCl buffer pH 7.5. The column was eluted either stepwise or by a linear salt gradient at a flow rate of 60 ml/h using a peristaltic pump. 50 ml DQ was introduced on the column and 300 drop (equivalent to approx. 5 ml) fractions were collected. Under these conditions, some of the substances in DQ passed unbound through the column, as will be seen from FIG. 2A (peak A). Elution was continued until no UV absorption was detectable. The absorption of the effluent liquid was recorded at 280 nm by a Uvicord II system (LKB-Produkter), and fractions were collected by a Golden Retriever (ISCO). At this point a buffer containing 0.2M NaCl made up in start buffer was introduced. As can be seen in FIG. 2A, a peak B is eluted. However, some substances were still attached to the bed material to such a degree that elution was difficult even with concentrated NaCl. These substances were the ones that contributed to the brownish colour of DQ, whereas peak A and B were only slightly coloured or completely colourless, respectively. In the next purification step, peak B was pooled and subjected to gel exclusion chromatography on Sephadex G50 fine equilibrated with M/50 phosphate buffer pH 7.5 in a K 16/70 column eluted at a flow rate of 10 ml/h. Desalting was carried out on Sephadex G25 medium in a K 16/40 column. Elution was carried out using a hydrostatic head of 50 cm. As will be seen from FIG. 2B, the UV profile showed 3 peaks. Peak C was eluted in the void volume (as determined by Blue Dextran 2000, Pharmacia Fine Chemicals) and peak E was eluted in the total volume of the column (also determined by potassium chromate). Peak D was well separated from peak C and E, but as can be seen in FIG. 2B, the presence of a shoulder indicated that peak D consisted of at least two substances.

Consequently, peak D was pooled and subjected to a new separation on DEAE-cellulose. The starting conditions were the same as in the first ion exchange experiment, and as a result all the material was adsorbed to the column. Elution was now continued with a linear NaCl gradient increasing from 0 to 1 molar (made up in the start buffer) in the course of 300 ml. The result of this experiment is shown in FIG. 2C. Two peaks F and G appeared in the UV profile. F was clearly separated and a single substance (section 3.3), but peak G could not be isolated since it was contaminated with F. In order to investigate the homogeneity of peak F, it was pooled, desalted on Sephadex G25, and rechromatographed in an identical experiment. As can be seen from FIG. 2D, only one symmetrical peak (H) appeared at the position of peak F.

Anyone of the fractions (also the DQ-extract) can be further purified as follows.

Figure 3:
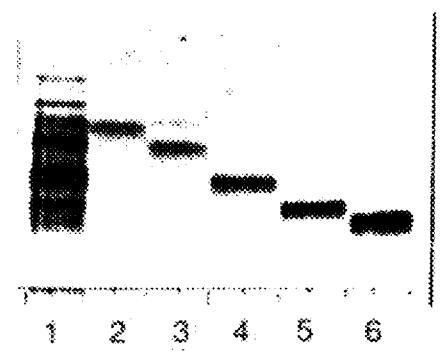
FIG. 3 demonstrates HPTLC-separation of Quil A and its subfractions.

Fraction H was lyophilized and dissolved in chloroform/methanol/$H_2O$ (60:40:9, v/v/v). 200 mg was then applied to an HPLC column (4.5×50 cm) packed with silicic acid, Iatrobeads RS-8060 (Iatron Labs, Tokyo, Japan). A pump speed of 5 ml/min was used for pumping a total of 2 L solvent, collecting 200 fractions of 10 ml with a gradient of chloroform/methanol/$H_2O$ (60:40:9 to 50:40:10) The fractions were analyzed with thin layer chromatography in the following way. 2 µl of every second fraction was analyzed by developing thin layer liquid chromatography plates (TLC-plates) (HPTLC, Merck, Bodman Chemicals, Gibbstown, N.J.) in chloroform/methanol/0.2% $CaCl_2$ (50:40:10 v/v/v) and the glycosides were determined by being greencoloured with anisaldehyde reagent (acetic acid/sulphoric acid/paraanisaldehyde (98:2:1)). The Quil A starting material was used as a reference of the $R_f$-value. (See FIG. 3, which shows a HPTLC-separation of: lane 1, Quil A (fraction H); lane 2, B1; lane 3, B2; lane 4: B3: lane 5, B4A; and lane 6, B4B).

Fractions that comigrate with B2, B3 and B4B having identical $R_f$-values were pooled and analyzed for purity with TLC. These crude fractions usually must be chromatographed two times in order to become pure enough. Fractions B1 and B4A are inactive and therefore are not separated further.

The thus enriched components were further purified on an HPLC column (21.2×250 mm) packed with 5µ spherical silica particles (Zorbax Si, DuPont, Wilmington, Del.). 40 mg enriched fraction B2, B3 or B4B dissolved in 1 ml chloroform/methanol/$H_2O$ (60:40;9 v/v/v) was put on the column. A pump speed of 3 ml/min was used for pumping a total of 0.9 l solvent, collecting 300 fractions of 3 ml with a gradient of chloroform/methanol/$H_2O$ (60:40;9 to 50;40;10 v/v/v). Fractions were analyzed on glass-backed HPLTC-plates as above. Purified fractions were pooled and evaporated to dryness in a rotary evaporator <30° C., dessiccated and stored in <−20° C. Approximately 20–25 rounds of this purification step was used i.e. using (20–25) ×200 mg=4–5 g Quil A starting material, including rechromatography to prepare 1 g of fraction B3. The yield of B2 and B4B was about 40% of the yield of B3.

The so prepared components B2, B3 and B4B were analyzed as follows.

a) Mass Spectrometry

Figure 4A:
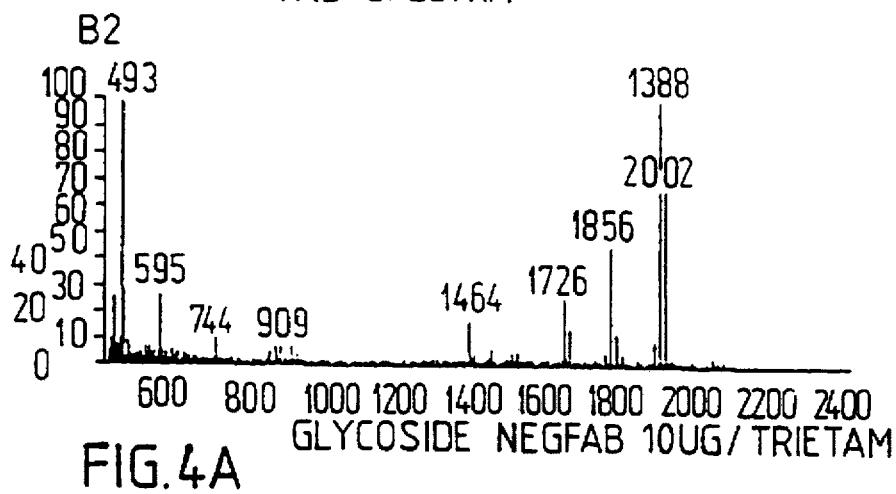
FIG. 4A shows the FAB-mass-spectrum for the new substance B2 according to the invention.
Figure 4B:
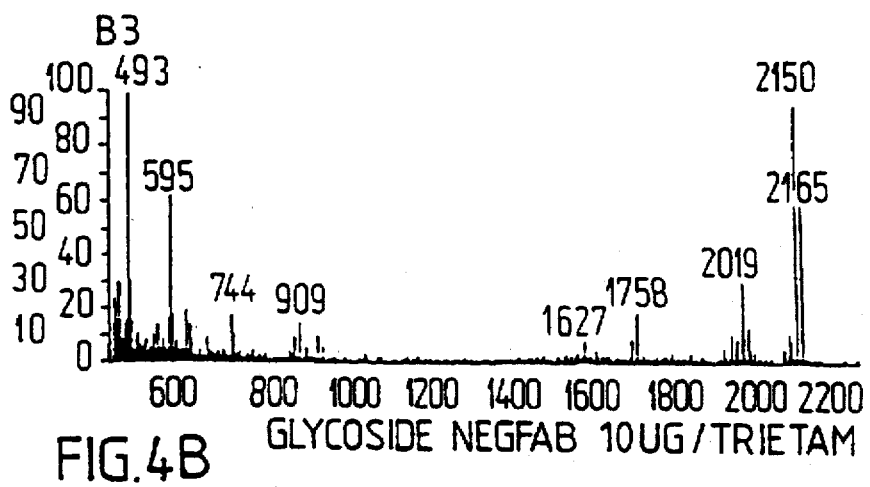
FIG. 4B shows the FAB-mass-spectrum for the new substance B3 according to the invention.
Figure 4C:
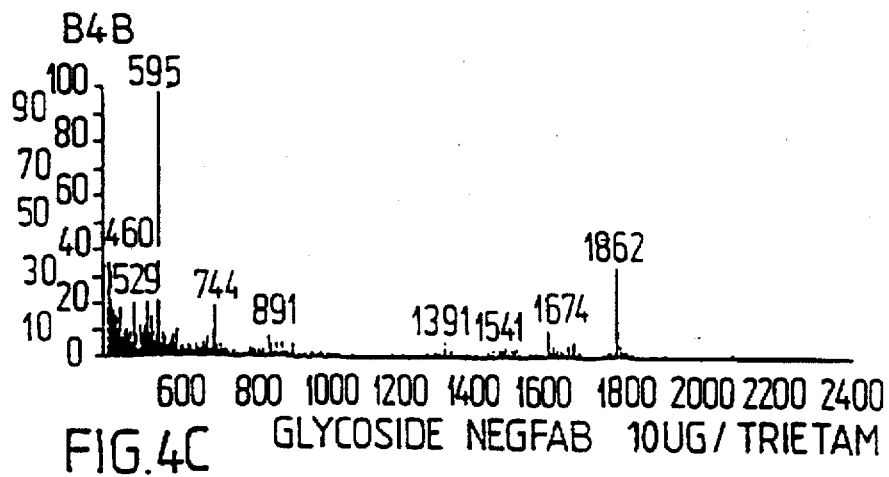
FIG. 4C shows the FAB-mass-spectrum for the new substance B4B according to the invention.
Figure 8:
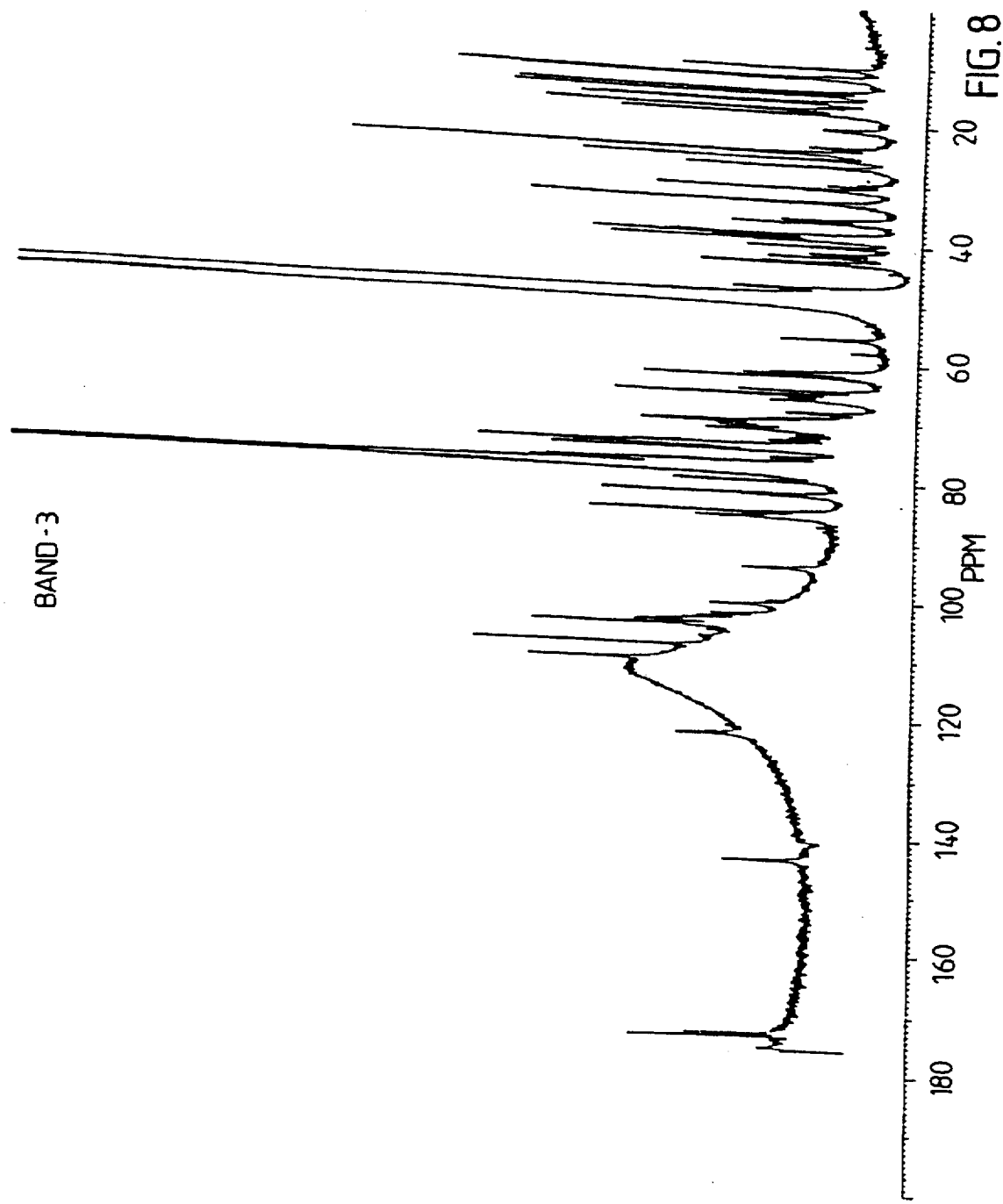
FIG. 8 shows the complete $^{13}$C-NMR-spectrum for the substance B3.
Figure 9:
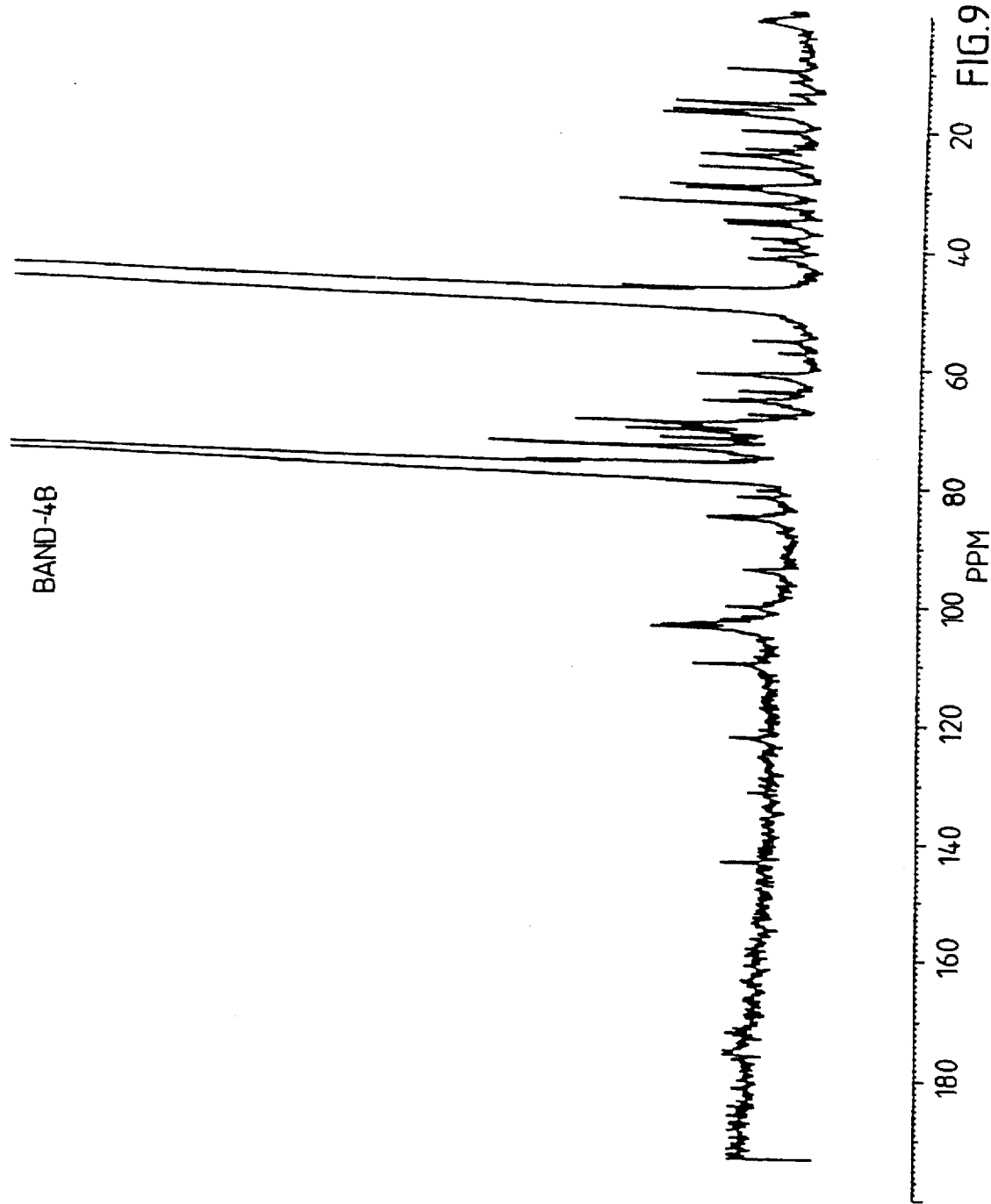
FIG. 9 shows the complete $^{13}$C-NMR-spectrum for the substance B4B.

Negative FAB-MS, FIG. 4, and positive FAB-MS (data not shown) were carried out for determination of molecular weights of the purified Quil A components B2, B3, B4A, and B4B. The data shown in FIG. 4 are preliminary and will have to be reacquired in a neutral pH matrix such as glycerol rather than in triethanolamine which was used for the spectra shown in FIG. 4. This is necessary because extreme alkalilability of the compounds, pH>8.5 have been demonstrated. Peaks at m/z 595, 744, and 893 stem from the matrix triethanolamine and should be disregarded. Our fraction B4A, which does not have any adjuvant or ISCOM particle forming capacity, seem to be identical with that described by Komori et al (for structure, see FIG. 10). The peaks corresponding to molecular weights of the three thus far most interesting glycosides are at: m/z 1988, B2; m/z 2150, B3; and m/z 1862, B4B.

b) $^{13}$C-NMR

FIGS. 5 and 6 show two regions, aliphatic carbon (8–45 ppm) and anomeric carbon (90–115 ppm), respectively, of the $^{13}$C-NMR spectra for the full size fractions: A, B2 (20 mg) B, B3 (80 mg); and C, B4B (40 mg). All spectra were obtained in the solvent-system, chloroform/methanol/water (30:60:8, v/v/v). The triterpenoid region is well resolved (8–45 ppm, FIG. 6) and has been partially assigned as seen in Table 4.

TABLE 4

Partial $^{13}$ C-NMR signal assignment (ppm) for β-amyrin five-ring segment of fractions B2, B3, and B4B (see FIG. 5) obtained in chloroform/methanol/water (30:60:8, v/v/v).

| Carbon# | B2 | B3 | B4B | Reference |
|---|---|---|---|---|
| C9[a] | -b | -b | -b | 45.5 |
| C10 | 36.4 | 36.2 | 36.3 | 37.0 |
| C12 | 122.5 | 122.5 | 122.5 | 123.1 |
| C13 | 144.1 | 146.6 | 143.6 | 144.8 |
| C14 | 41.5 | 41.8 | 41.9 | 41.6 |
| C15 | 30.0 | 30.5 | 30.7 | 30.7 |
| C18 | 43.0 | 42.8 | 41.9 | 42.7 |
| C20 | 30.7 | 30.6 | 30.6 | 30.7 |
| C25 | 16.0 | 16.1 | 16.0 | 15.9 |
| C26 | 17.7 | 17.3 | 17.6 | 17.6 |
| C29 | 32.9 | 32.9 | 32.9 | 32.2 |

[a]Numbered as in FIG. 5.
[b]Hidden under methanol signal of solvent (confirmed with a DEPT experiment).

Figure 10:
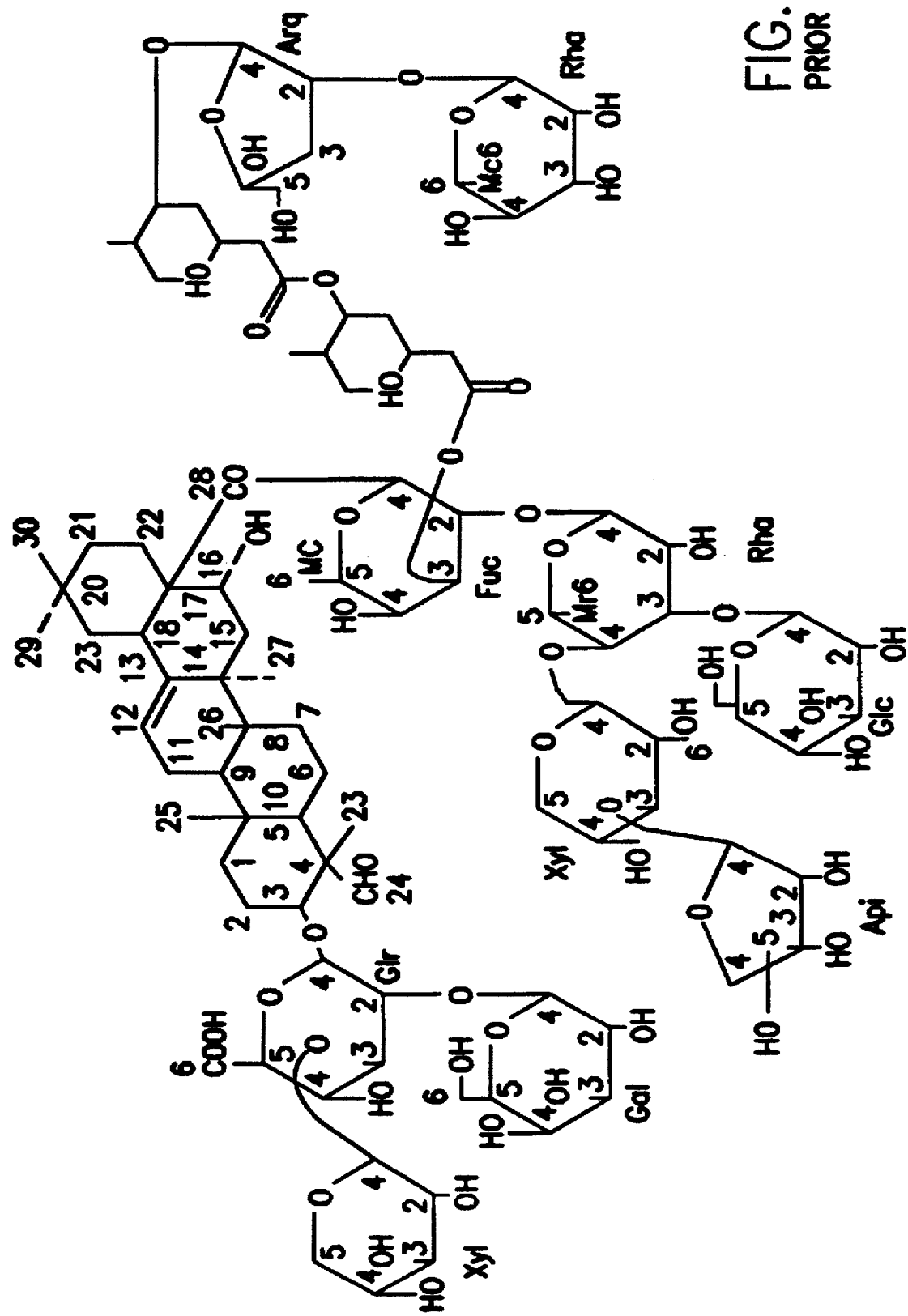

These assignments have been performed from studying a large number of reference-spectra obtained in various solvents and by analyzing the signals that are solvent-independent by a statistical comparison (data not shown). FIG. 6 shows the region between 80–148 ppm in the spectra of the three compounds, A, B2; B, B3; and C, B4B, featuring two double-bond carbon signals at 122 and 143 ppm corresponding to C-12 and C-13, respectively, in the β-amyrin skeleton (FIG. 10). The atomeric-carbon region, between 90–115 ppm, shows the presence of approximately 9–10 signals corresponding to the same amount of sugar-residues in the compounds.

Conclusion: Structural differences can be identified between fractions: A, B2; B, B3; and C, B4B, in both spectral regions corresponding to mainly the triterpenoid region and the oligosaccharide portions of the molecules, respectively. The exact amounts of sugars can not be determined at this point.

c) $^1$H NMR

FIG. 11 demonstrates the full proton spectrum (0–10 ppm) and FIG. 12 partial proton spectrum (anomeric region, 4.0–6.0 ppm), respectively, of fractions: A, B2 B. B3: and C, B4B. The spectra are obtained from samples (≈10 mg, ≈600 scans) dissolved in DMBO.$d_6$/$D_2O$ (98:2, v/v). To the far left in the spectrum (FIG. 11), at 9.4 ppm, the signal from the aldehyde proton on carbon-24 (see FIG. 5) is found. The doublet nature of this peak, a peak which is supposed to be a singlet, since it has no neighbouring protons to couple to, offers an explanation to the unusually complex anomeric region which is poorly resolved (as seen in the expansion in FIG. 12).

Figure 13A:
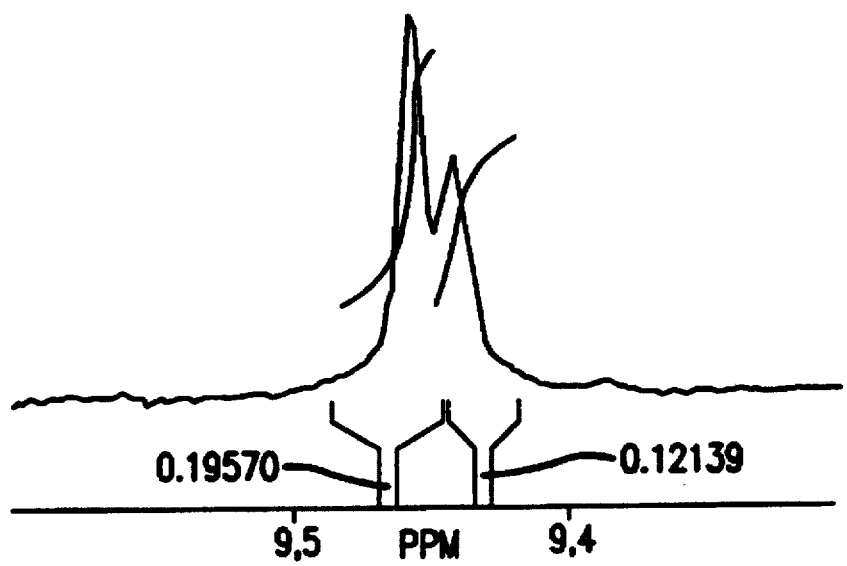
FIG. 13 shows parts of the spectra in FIGS. 7 and 8.
Figure 13B:
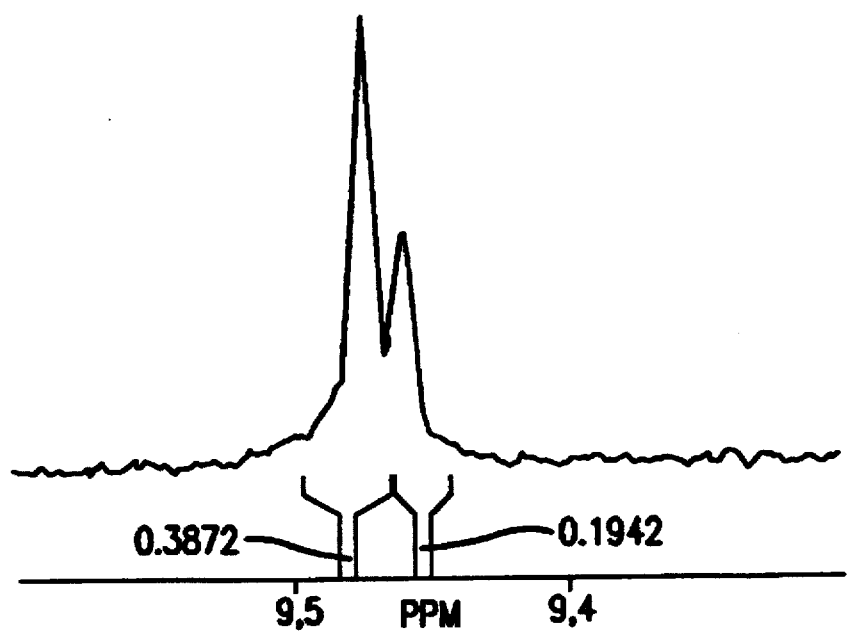

The doublet can be due to an aldehyde proton in two different compounds or to the presence of chemical exchange between two different populations of the same molecule (this process is slow enough in NMR time scale to be observed) thus explaining the different integrals of the peaks in the doublet at different temperatures as shown in FIG. 13 and Table 5.

TABLE 5

| Temperature in Degree K. | Shift 1 | Shift 2 | Difference in Shifts | Integral Quote Shift 1/Shift 2 |
|---|---|---|---|---|
| 301 | 9.46 | 9.44 | 0.02 | 1.61 |
| 351 | 9.47 | 9.46 | 0.01 | 1.99 |
| 361 | 9.48 | 9.47 | 0.01 | 2.23 |

FIG. 13 and Table 5 (above) demonstrate that the relative integral of the peaks varies with temperature and that the two peaks move closer to each other at a higher temperature, both indicating that it can not be two different molecules but rather two different populations of the same molecule. This would explain the complex anomeric region by suggesting that many atomeric protons in the molecule would have double resonances due to different chemical environments in the two populations. However, the present set of data indicates that differences in the glycosylation of the compounds could provide part of the explanation of their structural differences (FIG. 12), by demonstrating different amount of anomeric proton signals in the spectra. The FAB-MS data for fractions B2, B3 and B4B also does not rule out the formal possibility that two similar size molecules, with very similar physico-chemical properties, exist that have the same amount of sugars but differ in linkage-positions and/or sequence.

Figure 14:
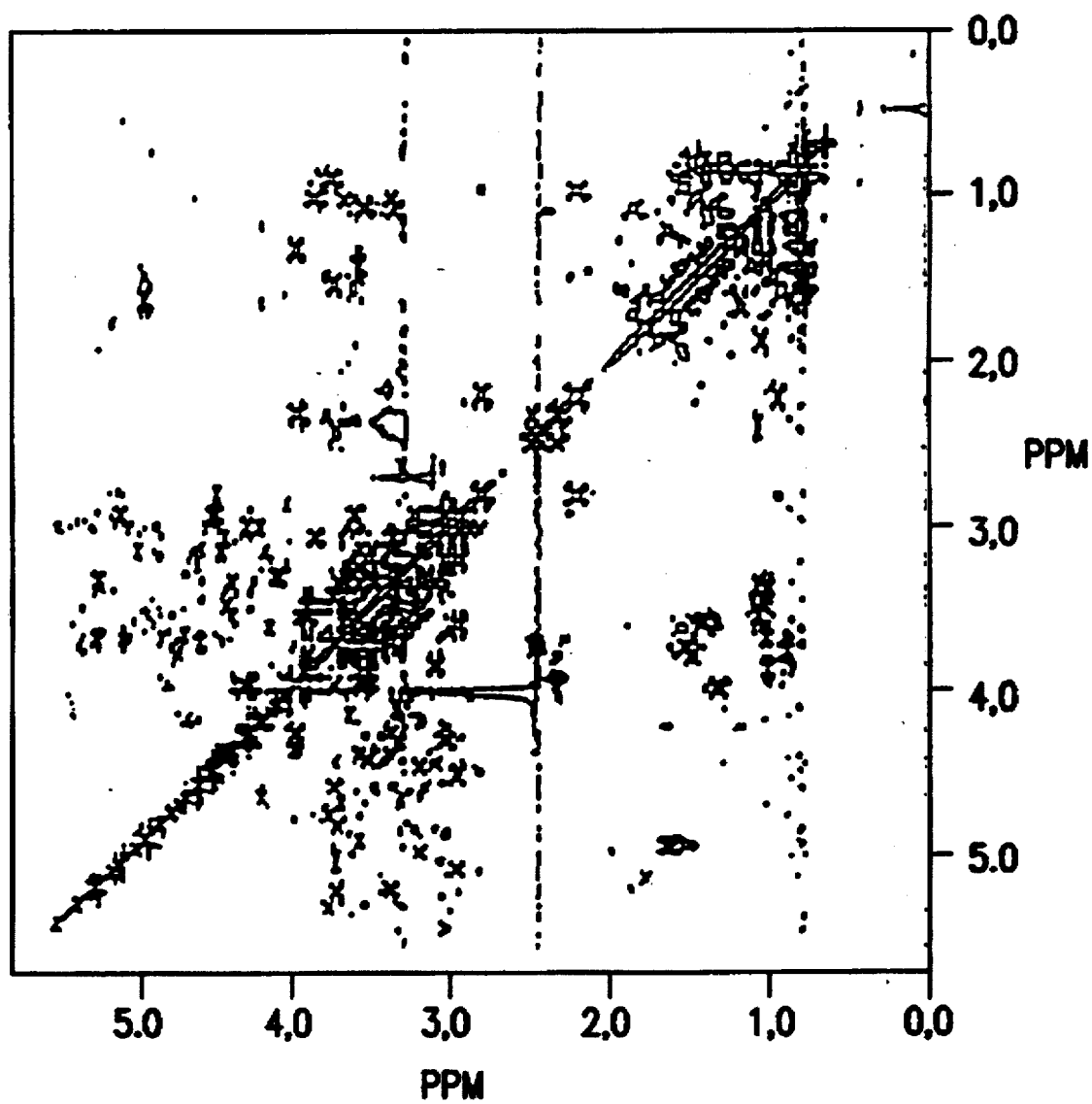
FIG. 14 shows a 2-dimensional E-spectrum for substance B3.

Conclusion: In general, 1-dimensional $^1$H NMR spectra from 8–10 sugar containing earlier unknown molecules are not sufficient for assignment of protons and detailed structural characterization. For resolving all signals and for making proper assignments through out the compounds it will be necessary to use the 2-dimensional NMR technique as well as chemically degrade the compounds for analysis. Both homonuclear ($^1$H-$^1$H) and heteronuclear ($^1$H-$^{13}$H) COSY, TOCSY as well as NOESY. The 2-dimensional proton phase sensitive correlation double quantum filtered NMR spectrum (DQFPSCOSY) for fraction B3 is shown in FIG. 14.

d) Summary of Structural Data

The conclusion of data generated thus far is that the active fractions that have adjuvant activity and ISCOM particle forming capacity in Quil A contain unique glycosylated triterpenoid-saponins that differ between each other in both their triterpenoid and glycan parts. They have an approximate structure like the one described in FIG. 10 and consist of a five-ring steroid skeleton of β-amyrin type and contains 8–11 sugar residues.

EXAMPLE 7

0.1 mg cholesterol was mixed with $^3$H-cholesterol (10 mg/ml dissolved in 20% MEGA-10 in $H_2O$) and 0.5 mg B2 or B3 or B4B or mixtures thereof. The volume was adjusted to 0.5 ml and the mixture dialysed against PBS on a preparation treated with ammonium molybdate (negative colouring technique). The dialysed preparations were analysed for the presence of complex with iscom structure by electron microscopy (EM) and analytical gradient centrifugation. In EM the iscom structure is characterized by a cage-like particle with a diameter of 40 nm composed of subunits with annular structure with a diameter of 12 nm. For sedimentation studies the sample is placed over a sacharose gradient (10–50%) and centrifuged for 18 hours, +10° C. in a TST 41,14 rotor, 40 000 rpm. The gradient is collected in 18 fractions (fraction 1=the bottom and fraction 18=the top). By localizing the 3H-cholesterol activity in the gradient, one can tell the sedimentation constant and see if complexes have been made. B4B forms typical iscom structures with cholesterol but has no potent adjuvant activity.

B2 does not form iscom-like structures with cholesterol but binds to cholesterol. Together with B4B, B2 forms iscom-like structures with cholesterol. B2 has a weak adjuvant activity.

B3 binds to cholesterol but not in iscom-like structures. With B4B, B3 like B2, can form iscom-like structures with cholesterol. B3 has adjuvant activity.

We claim:

1. A vaccine comprising an immunomodulating agent having an iscom-like structure and comprising within said iscom-like structure at least one lipid and at least one saponin, said iscom-like structure being free of incorporated antigens; one or more antigens in admixture with said immunomodulating agent but not integrated into said iscom-like structure; and a pharmaceutically acceptable vehicle.

2. A kit for human or veterinary medical use, comprising: (a) an immunomodulating agent having an iscom-like structure and comprising within said iscom-like structure at least one lipid and at least one saponin, said iscom-like structure being free of incorporated antigens; and (b) one or more immunomodulating substances and a pharmaceutically acceptable vehicle; said components (a) and (b) being confined in separate containers.

3. A method of inducing an immunomodulatory response in a patient in need thereof, comprising administering (a) an antigenically effective amount of at least one antigen, and (b) an immunomodulating agent in an amount effective to produce an immunomodulatory effect on the action of said at least one antigen, said immunomodulating agent having an iscom-like structure and comprising within said iscom-like structure at least one lipid and at least one saponin, said iscom-like structure being free of incorporated antigens; said components (a) and (b) being administered in admixture, or separately.

4. The method according to claim 3, wherein said at least one antigen is in multimeric form.

5. The method according to claim 3, wherein said at least one lipid is a sterol.

6. The method according to claim 5, wherein said sterol is cholesterol.

7. The method according to claim 3, wherein said at least one saponin is a triterpensaponin.

8. The method according to claim 7, wherein said triterpensaponin is Quil A.

9. A kit for human or veterinary medical use, comprising: (a) an immunomodulating agent having an iscom-like structure and comprising within said iscom-like structure at least one lipid and at least one saponin, said iscom-like structure being free of incorporated antigens; and (b) one or more immunomodulating substances and a pharmaceutically acceptable vehicle; said components (a) and (b) being in admixture in a single container.

Figure 11A:
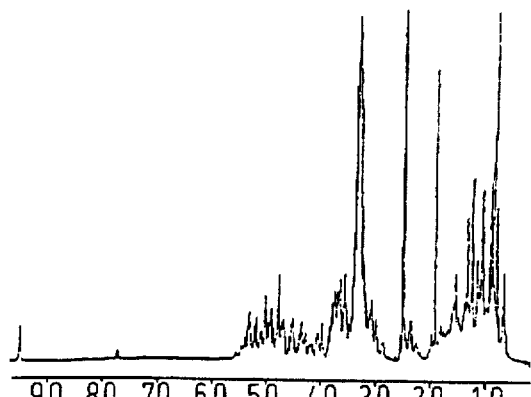
FIG. 11A shows the $^1$H NMR-spectrum in a first region for the new substance B2.
Figure 12A:
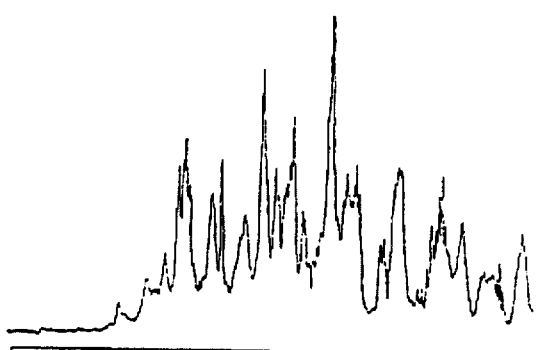
FIG. 12A shows the $^1$H NMR-spectrum in a second region for the new substance B2.
Figure 11B:
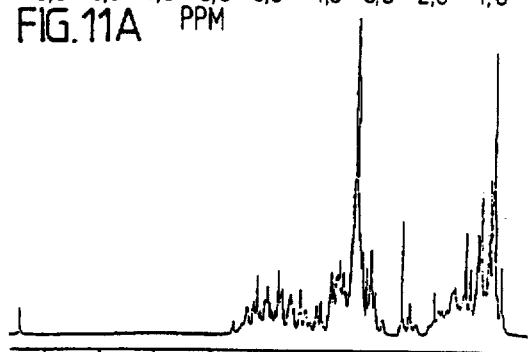
FIG. 11B shows the $^1$H NMR-spectrum in a first region for the new substance B3.
Figure 12B:
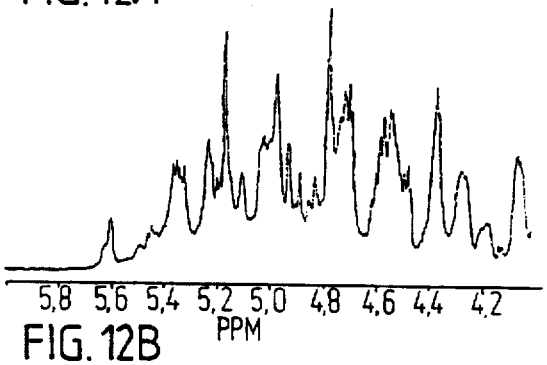
FIG. 12B shows the $^1$H NMR-spectrum in a second region for the new substance B3.
Figure 11C:
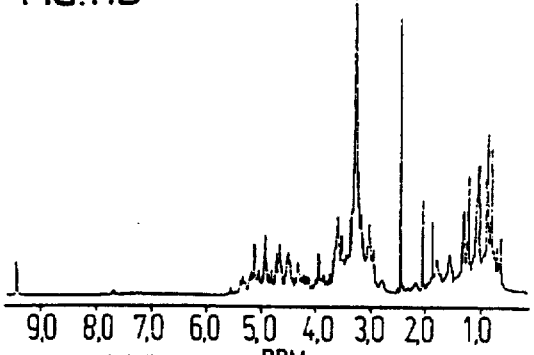
FIG. 11C shows the $^1$H NMR-spectrum in a first region for the new substance B4B.
Figure 12C:
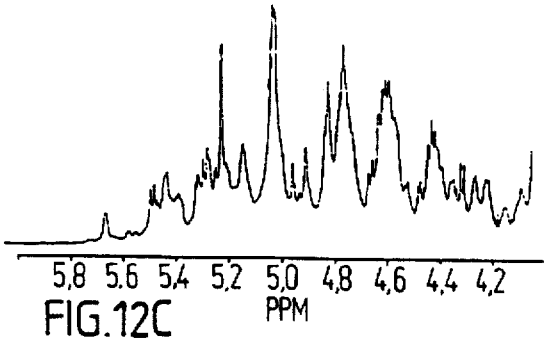
FIG. 12C shows the $^1$H NMR-spectrum in a second region for the new substance B4B.

10. The vaccine according to claim 16, wherein said saponin is isolated from Quillaja Saponaria Molina of β-amyrin type with 8–11 carbohydrate moieties, and is selected from the group consisting of:

a) substance B2 having a molecular weight of 1988, a carbon 13 NMR spectrum as shown in FIGS. 5A and 6A, and a proton NMR spectrum as shown in FIGS. 11A and 12A;

b) substance B3 having a molecular weight of 2150 and a carbon 13 NMR spectrum as shown in FIGS. 5B and 6B, and a proton NMR spectrum as shown in FIGS. 11B and 12B; and c) substance B4B having a molecular weight of 1862, a carbon 13 NMR spectrum as shown in FIGS. 5C and 6C, and a proton NMR structure as shown in FIGS. 11C and 12C.

* * * * *